United States Patent
Becking et al.

(10) Patent No.: US 9,949,816 B2
(45) Date of Patent: Apr. 24, 2018

(54) IVC FILTER RETRIEVAL SYSTEMS WITH MULTIPLE CAPTURE MODES

(71) Applicant: AVANTEC VASCULAR CORPORATION, Sunnyvale, CA (US)

(72) Inventors: Frank Becking, Sunnyvale, CA (US); Kathryn A. Stecco, Sunnyvale, CA (US); Teresa Ruvalcaba, Sunnyvale, CA (US); Karl Halden, Sunnyvale, CA (US)

(73) Assignee: AVANTEC VASCULAR CORPORATION, Sunnyvale, CA (US)

( * ) Notice: Subject to any disclaimer, the term of this patent is extended or adjusted under 35 U.S.C. 154(b) by 0 days.

(21) Appl. No.: 14/965,749

(22) Filed: Dec. 10, 2015

(65) Prior Publication Data
US 2016/0095689 A1    Apr. 7, 2016

Related U.S. Application Data

(63) Continuation-in-part of application No. PCT/US2014/042343, filed on Jun. 13, 2014.

(60) Provisional application No. 61/835,295, filed on Jun. 14, 2013.

(51) Int. Cl.
| | |
|---|---|
| *A61F 2/01* | (2006.01) |
| *A61B 17/221* | (2006.01) |
| *A61B 17/22* | (2006.01) |
| *A61M 25/00* | (2006.01) |

(52) U.S. Cl.
CPC .............. *A61F 2/01* (2013.01); *A61B 17/221* (2013.01); *A61F 2/013* (2013.01); *A61M 25/0012* (2013.01); *A61B 2017/2215* (2013.01); *A61B 2017/22035* (2013.01); *A61F 2002/011* (2013.01); *A61F 2002/016* (2013.01); *A61F 2210/0014* (2013.01); *A61M 2025/0096* (2013.01)

(58) Field of Classification Search
CPC ............ A61B 17/221; A61B 17/22031; A61B 2017/2212; A61B 2017/2217; A61B 2017/2215; A61B 2017/22035; A61F 2002/011; A61F 2002/016; A61F 2/013
See application file for complete search history.

(56) References Cited

U.S. PATENT DOCUMENTS

| | | | |
|---|---|---|---|
| 3,952,737 | A | 4/1976 | Kimmell, Jr. |
| 4,085,743 | A | 4/1978 | Yoon |
| 4,174,715 | A | 11/1979 | Hasson |

(Continued)

FOREIGN PATENT DOCUMENTS

| | | |
|---|---|---|
| EP | 1172073 A1 | 1/2002 |
| JP | H 10-509623 A | 9/1998 |

(Continued)

OTHER PUBLICATIONS

WO, PCT/US2014/042343 ISR, dated Sep. 30, 2014.
(Continued)

*Primary Examiner* — Christopher L Templeton
(74) *Attorney, Agent, or Firm* — One LLP

(57) ABSTRACT

Funnel-trap type delivery and/or retrieval devices for temporary Inferior Vena Cava (IVC) filters or other medical implants or foreign bodies are described. These may employ a locking sheath or a proximal-aperture capture feature or features for IVC filter (or other device) retrieval.

22 Claims, 4 Drawing Sheets

(56) References Cited

U.S. PATENT DOCUMENTS

| | | |
|---|---|---|
| 4,467,802 A | 8/1984 | Maslanka |
| 4,611,594 A | 9/1986 | Grayhack et al. |
| 4,655,219 A | 4/1987 | Petruzzi |
| 4,723,936 A | 2/1988 | Buchbinder et al. |
| 4,873,978 A | 10/1989 | Ginsburg |
| 4,960,411 A | 10/1990 | Buchbinder |
| 5,011,488 A | 4/1991 | Ginsburg |
| 5,041,093 A * | 8/1991 | Chu .............. A61B 17/221 604/104 |
| 5,074,845 A | 12/1991 | Miraki et al. |
| 5,098,440 A | 3/1992 | Hillstead |
| 5,102,415 A | 4/1992 | Guenther et al. |
| 5,549,626 A | 8/1996 | Miller et al. |
| 5,601,595 A | 2/1997 | Smith |
| 5,653,684 A | 8/1997 | Laptewicz et al. |
| 5,662,671 A | 9/1997 | Barbut et al. |
| 5,746,251 A * | 5/1998 | Bullard ............... F16K 7/02 137/625.12 |
| 5,782,747 A | 7/1998 | Zimmon |
| 5,800,457 A | 9/1998 | Gelbfish |
| 5,814,064 A | 9/1998 | Daniel et al. |
| 5,827,324 A | 10/1998 | Cassell et al. |
| 5,846,251 A | 12/1998 | Hart |
| 5,908,435 A | 6/1999 | Samuels |
| 5,911,734 A | 6/1999 | Tsugita et al. |
| 5,944,728 A | 8/1999 | Bates |
| 6,001,118 A | 12/1999 | Daniel et al. |
| 6,159,230 A | 12/2000 | Samuels |
| 6,203,561 B1 | 2/2001 | Ramee et al. |
| 6,210,370 B1 * | 4/2001 | Chi-Sing ........... A61B 17/22032 604/104 |
| 6,238,412 B1 | 5/2001 | Dubrul et al. |
| 6,251,092 B1 | 6/2001 | Qin et al. |
| 6,251,122 B1 | 6/2001 | Tsukernik |
| 6,264,671 B1 | 7/2001 | Stack et al. |
| 6,273,900 B1 | 8/2001 | Nott et al. |
| 6,290,710 B1 | 9/2001 | Cryer et al. |
| 6,306,163 B1 | 10/2001 | Fitz |
| 6,336,934 B1 | 1/2002 | Gilson et al. |
| 6,395,017 B1 | 5/2002 | Dwyer et al. |
| 6,443,972 B1 | 9/2002 | Bosma et al. |
| 6,447,531 B1 | 9/2002 | Amplatz |
| 6,458,151 B1 | 10/2002 | Saltiel |
| 6,485,501 B1 | 11/2002 | Green |
| 6,500,182 B2 | 12/2002 | Foster |
| 6,569,184 B2 | 5/2003 | Huter |
| 6,602,271 B2 | 8/2003 | Adams et al. |
| 6,605,102 B1 | 8/2003 | Mazzocchi et al. |
| 6,632,236 B2 | 10/2003 | Hogendijk |
| 6,645,222 B1 | 11/2003 | Parodi et al. |
| 6,663,652 B2 | 12/2003 | Daniel et al. |
| 6,679,893 B1 | 1/2004 | Tran |
| 6,695,813 B1 | 2/2004 | Boyle et al. |
| 6,699,260 B2 | 3/2004 | Dubrul et al. |
| 6,702,834 B1 | 3/2004 | Bpylan et al. |
| 6,743,247 B1 | 6/2004 | Levinson et al. |
| 6,780,196 B2 | 8/2004 | Chin et al. |
| 6,800,080 B1 * | 10/2004 | Bates ............... A61B 17/221 606/127 |
| 6,833,002 B2 | 12/2004 | Stack et al. |
| 6,896,690 B1 | 5/2005 | Lambrecht et al. |
| 6,958,074 B2 | 10/2005 | Russell |
| 7,211,089 B2 | 5/2007 | Kear et al. |
| 7,322,989 B2 | 1/2008 | Teague et al. |
| 7,338,512 B2 | 3/2008 | McGuckin, Jr. et al. |
| 7,377,925 B2 | 5/2008 | Poll |
| 7,491,210 B2 | 2/2009 | Dubrul et al. |
| 7,625,390 B2 | 12/2009 | Hendriksen et al. |
| 7,658,747 B2 | 2/2010 | Forde et al. |
| 7,731,723 B2 | 6/2010 | Kear et al. |
| 7,780,693 B2 | 8/2010 | Brady et al. |
| 7,780,694 B2 | 8/2010 | Palmer et al. |
| 7,837,702 B2 | 11/2010 | Bates |
| 7,993,362 B2 | 8/2011 | Lowe et al. |
| 8,038,704 B2 | 10/2011 | Sherburne |
| 8,043,322 B2 | 10/2011 | Hendriksen et al. |
| 8,163,004 B2 | 4/2012 | Amplatz et al. |
| 8,202,309 B2 | 6/2012 | Styrc |
| 8,273,073 B2 | 9/2012 | Levine et al. |
| 8,298,244 B2 | 10/2012 | Garcia et al. |
| 8,469,969 B2 | 6/2013 | Kear et al. |
| 8,469,970 B2 | 6/2013 | Diamant |
| 8,475,488 B2 | 7/2013 | Cartier et al. |
| 8,512,401 B2 | 8/2013 | Murray, III et al. |
| 8,747,597 B2 | 6/2014 | Rosqueta et al. |
| 2001/0044595 A1 * | 11/2001 | Reydel ............. A61F 2/95 604/98.02 |
| 2002/0010476 A1 | 1/2002 | Mulholland et al. |
| 2002/0062135 A1 | 5/2002 | Mazzocchi et al. |
| 2002/0068967 A1 | 6/2002 | Drasler et al. |
| 2002/0169474 A1 | 11/2002 | Kusleika et al. |
| 2003/0176884 A1 * | 9/2003 | Berrada ............. A61F 2/013 606/200 |
| 2003/0187474 A1 * | 10/2003 | Keegan ............. A61F 2/0095 606/200 |
| 2004/0049226 A1 | 3/2004 | Keegan et al. |
| 2004/0093012 A1 * | 5/2004 | Cully ............... A61F 2/013 606/200 |
| 2004/0138677 A1 | 7/2004 | Little et al. |
| 2004/0153118 A1 | 8/2004 | Clubb et al. |
| 2004/0181237 A1 | 9/2004 | Forde et al. |
| 2004/0199202 A1 * | 10/2004 | Dubrul ............. A61B 10/0266 606/200 |
| 2005/0159770 A1 | 7/2005 | Divani et al. |
| 2005/0182439 A1 | 8/2005 | Lowe |
| 2005/0187570 A1 * | 8/2005 | Nguyen ............ A61B 17/221 606/159 |
| 2005/0234502 A1 | 10/2005 | Gilson et al. |
| 2005/0267515 A1 | 12/2005 | Oliva et al. |
| 2006/0020256 A1 | 1/2006 | Bell et al. |
| 2006/0074446 A1 | 4/2006 | Gilson et al. |
| 2006/0247572 A1 | 11/2006 | McCartney |
| 2007/0005101 A1 | 1/2007 | Fahey et al. |
| 2007/0112374 A1 * | 5/2007 | Paul, Jr. ............ A61F 2/013 606/200 |
| 2007/0149996 A1 * | 6/2007 | Coughlin ........... A61F 2/013 606/200 |
| 2007/0173884 A1 | 7/2007 | Gilson et al. |
| 2007/0244504 A1 | 10/2007 | Keegan et al. |
| 2007/0282369 A1 | 12/2007 | Gilson et al. |
| 2008/0091223 A1 | 4/2008 | Pokorney et al. |
| 2009/0182370 A1 | 7/2009 | Volobuyev et al. |
| 2009/0192485 A1 | 7/2009 | Heuser |
| 2009/0198315 A1 | 8/2009 | Boudjemline |
| 2009/0222035 A1 | 9/2009 | Schneiderman |
| 2009/0222076 A1 | 9/2009 | Figulla et al. |
| 2009/0248060 A1 * | 10/2009 | Schneider .......... A61F 2/013 606/200 |
| 2009/0287291 A1 | 11/2009 | Becking et al. |
| 2010/0137846 A1 * | 6/2010 | Desai ............... A61B 17/221 606/2.5 |
| 2010/0256669 A1 | 10/2010 | Harris et al. |
| 2010/0312268 A1 | 12/2010 | Belson |
| 2010/0331949 A1 | 12/2010 | Habib |
| 2011/0040321 A1 | 2/2011 | Cartier |
| 2011/0046611 A1 | 2/2011 | Christiansen |
| 2011/0125180 A1 | 5/2011 | Tripp et al. |
| 2011/0178547 A1 | 7/2011 | Paul, Jr. et al. |
| 2011/0282274 A1 | 11/2011 | Fulton, III |
| 2011/0288572 A1 * | 11/2011 | Martin .............. A61B 17/221 606/159 |
| 2011/0307002 A1 | 12/2011 | Gilson et al. |
| 2012/0041473 A1 | 2/2012 | Nigon |
| 2013/0197567 A1 * | 8/2013 | Brady ............... A61B 17/221 606/200 |
| 2013/0267848 A1 | 10/2013 | Fearmot et al. |
| 2013/0289694 A1 | 10/2013 | Sherburne |
| 2014/0005712 A1 * | 1/2014 | Martin .............. A61B 17/221 606/200 |
| 2014/0024887 A1 | 1/2014 | Ishii et al. |
| 2014/0155930 A1 | 6/2014 | Bennett et al. |
| 2014/0373334 A1 | 12/2014 | Gamarra et al. |

(56) References Cited

U.S. PATENT DOCUMENTS

| | | |
|---|---|---|
| 2015/0105819 A1 | 4/2015 | Becking et al. |
| 2015/0366650 A1 | 12/2015 | Zi et al. |
| 2016/0296315 A1 | 10/2016 | Yachia et al. |

FOREIGN PATENT DOCUMENTS

| | | |
|---|---|---|
| JP | 2003-501203 A | 1/2003 |
| JP | 2004-524049 A | 8/2004 |
| JP | 2005-523767 A | 8/2005 |
| JP | 2007-508902 A | 4/2007 |
| JP | 2008-513121 A | 5/2008 |
| JP | 2008-514276 A | 5/2008 |
| JP | 4109422 B2 | 7/2008 |
| JP | 2009-517124 A | 4/2009 |
| JP | 4320142 B2 | 8/2009 |
| JP | 2013-154183 A | 8/2013 |
| KR | 101133157 B1 | 4/2012 |
| WO | WO 00/16846 A1 | 3/2000 |

OTHER PUBLICATIONS

WO, PCT/U52014/042343 IPRP, dated Dec. 15, 2015.
WO, PCT/US2015/065102 ISR and Written Opinion, dated Sep. 8, 2016.
US, U.S. Appl. No. 14/569,500 Office Action, dated Nov. 3, 2016.
WO, PCT/US2015/058898 ISR and Written Opinion, dated Feb. 11, 2016.
WO, PCT/US2015/065074 ISR and Written Opinion, dated Mar. 22, 2016.
WO, PCT/US2015/065025 ISR and Written Opinion, dated Apr. 1, 2016.
EP, 14810754.3 Extended Search Report, dated Nov. 24, 2016.

* cited by examiner

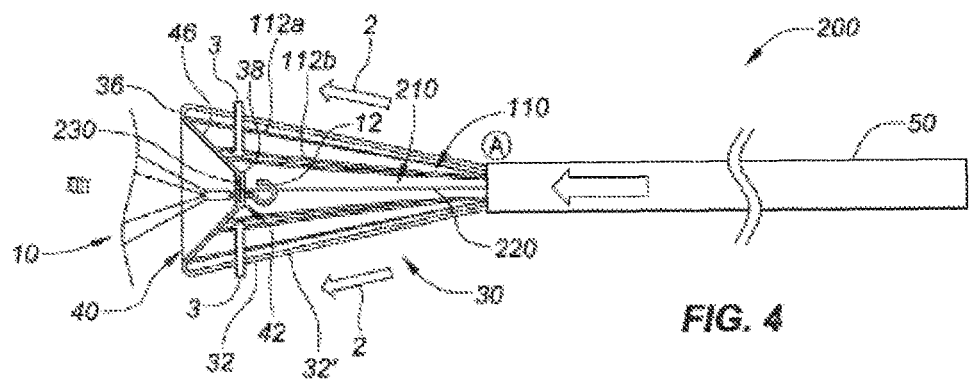
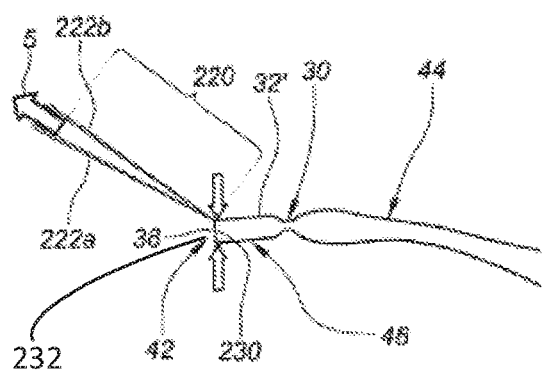
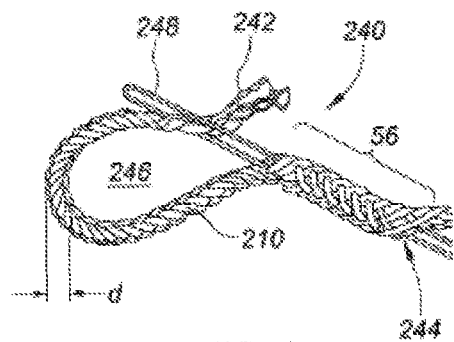
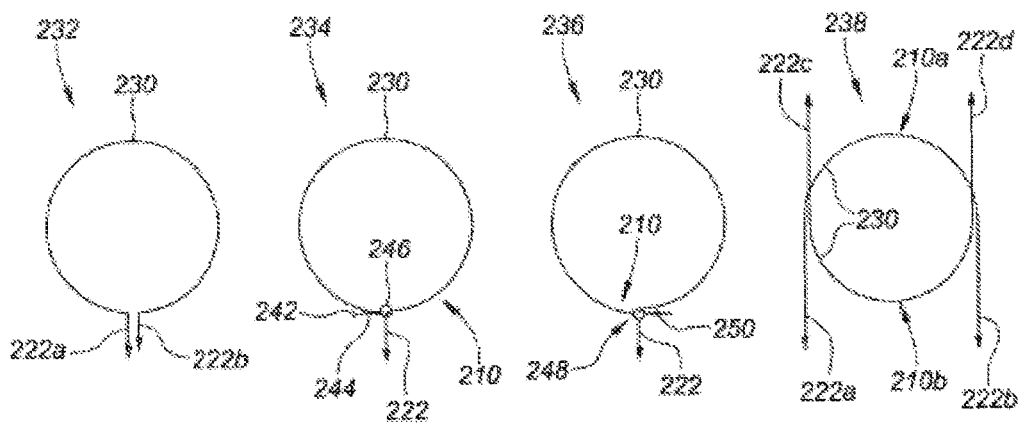
FIG. 4
FIG. 5
FIG. 6
FIG. 7A  FIG. 7B  FIG. 7C  FIG. 7D

IVC FILTER RETRIEVAL SYSTEMS WITH MULTIPLE CAPTURE MODES

RELATED APPLICATIONS

This application is a continuation-in-part of International Patent Application PCT/US2014/042343 filed Jun. 13, 2014, which claims priority to U.S. Provisional Application No. 61/835,295 filed Jun. 14, 2013, all of which are incorporated by reference herein in their entirety and for all purposes.

FIELD

The embodiments described herein relate to endovascular temporary Inferior Vena Cava (IVC) filter, other implant or other foreign body retrieval devices or system and methods.

BACKGROUND

Temporary IVC filters are placed much like permanent filters, but are designed so that they may be retrieved in a separate endovascular procedure, generally from a femoral vein or internal jugular vein approach. Most of the currently available temporary filters include a hook-like feature with which they can be captured and received within a catheter or sheath for removal by employing a gooseneck snare or a multi-loop snare.

While retrieval is a simple procedure in principle, difficulty is often encountered capturing a filter's hook with the snare loop(s). Such difficulty is compounded when the filter is tilted or off-kilter in placement. Several filters are designed to avoid such orientation. However, the problem remains common because the device is not anchored into the IVC in a stable fashion. Constant blood flow in addition to blood clots can disorient the filter within the IVC making recapture difficult. Accordingly, there exists a need for a filter retrieval system with improved ease of use and/or less susceptibility to problems of filter orientation.

SUMMARY

Embodiments hereof meet this need and others as applied to other medical device applications. For IVC filters, the subject systems may be used with a wide variety of filter architectures—existing or otherwise. Accordingly, new filters may be designed for use with the subject retrievers in which fewer design constraints and/or compromises may be required of the filter design. Features of the subject system may be used in connection with existing and/or modified versions of the filters described in any of U.S. Pat. Nos. 3,952,747; 5,601,595; 6,443,972; 7,338,512 and 7,625,390 (all of which patents are incorporated herein by reference in their entireties for any purpose), with commercially available devices including the OPTEASE, GÜNTHER TULIP, CELECT and OPTION or others.

Embodiments hereof share a "funnel-trap" type architecture. This is advantageously constructed of heatset braid, possibly superelastic (SE) nickel-titanium alloy (Nitinol) braid. The funnel-trap end of a retrieval device includes a distal rim defining a distal opening, and a more proximal aperture or opening. A pocket is formed between the proximal opening and sides of the braid (or other material from which the device is constructed).

When an enlarged proximal end of an IVC filter or other implant is guided past the distal rim of the funnel shape it passes through the proximal opening for capture. Such an enlargement by be in the form of a nubbin or bump or a hook-type interface. In one example a locking sheath is advanced over and closes the trap to secure the enlarged end of the medical device in a pocket adjacent to the proximal opening or aperture. In another embodiment, the proximal aperture is cinched closed to effect capture. In yet another embodiment, crossing members act like a web to catch or entangle any hook or other feature passing into or through the proximal opening aperture.

The subject delivery and/or retrieval devices, kits in which they are included (with and without assembly), methods of use and manufacture (including assembly of the constituent components in vivo or ex vivo) are all included within the scope of the present disclosure. Some aspects of the same are described above, and more detailed discussion is presented in connection with the figures below.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 4 is a partial side-sectional view of retrieval system embodiment including a loop and tether.

FIG. 5 is a side view of a partially inverted preform and associated tether or loop.

FIG. 6 is a side view of a portion of a tether and setup for splicing.

FIGS. 7A-7D are top or end view illustrations of various loop and tether construction options.

DETAILED DESCRIPTION

Various exemplary embodiments are described below. Reference is made to these examples in a non-limiting sense, as it should be noted that they are provided to illustrate more broadly applicable aspects of the devices, systems and methods. Various changes may be made to these embodiments and equivalents may be substituted without departing from the true spirit and scope of the various embodiments. In addition, many modifications may be made to adapt a particular situation, material, composition of matter, process, process act(s) or step(s) to the objective(s), spirit or scope of the present invention. All such modifications are intended to be within the scope of the claims made herein.

Before the present subject matter is described in detail, it is to be understood that this disclosure is not limited to the particular example embodiments described, as such may, of course, vary. It is also to be understood that the terminology used herein is for the purpose of describing particular embodiments only, and is not intended to be limiting, since the scope of the present disclosure will be limited only by the appended claims.

Figure 1A:
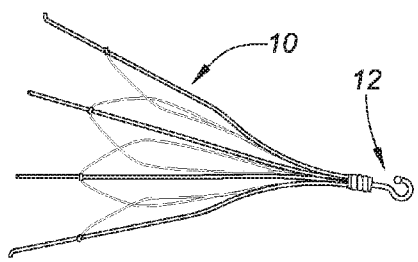
FIGS. 1A and 1B picture IVC filter variations as may be used in the present system.
Figure 1B:
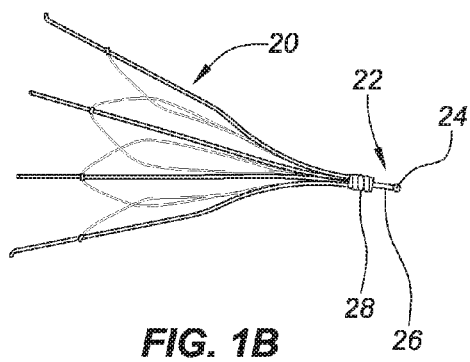
Figure 2:
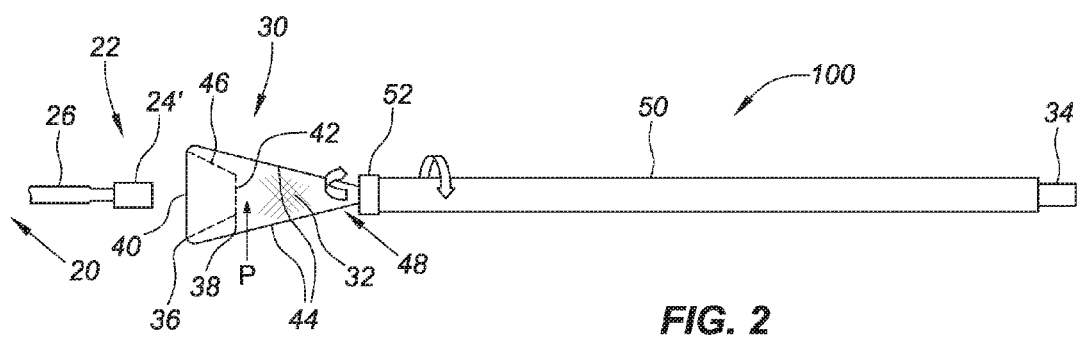
FIG. 2 is a side view of a delivery and/or retrieval system with an end of any type of implantable medical device or foreign body.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description FIG. 1A shows a GÜNTHER TULIP (Cook Medical, Inc.) temporary IVC filter 10 with a hook 12 end interface for retrieval. As shown in FIG. 1B for a IVC filter 20, the hook may be modified or substituted for a nubbin-type interface 22. The nubbin (itself) may comprise a laser-formed or solder-formed protuberance or bump 24 on an extension 26 from a hub 28. Alternatively, as shown in FIG. 2, a/the filter retrieval interface 22 may comprise a band 24' (e.g., a Pt marker band) mounted (e.g., by swaging, welding, gluing, etc.) on a/the extension 26. However the enlargement is created, the funnel-trap structures described below are adapted to secure that feature for IVC filter retrieval.

FIG. 2 provides an overview of the subject system 100. A funnel-trap structure 30 is shown made of heatset braid material 32. The construction provides a flexible distal extension to an elongate shaft 34. The shaft is received within an elongate sleeve 50 (that may be a commercially available catheter or sheath or a custom part of the overall system 100) and may include a distal radiopaque marker band 52.

The braid may comprise Nitinol (preferably that is superelastic (SE) at human body temperature), CoCr, Stainless Steel or another biocompatible material. It is advantageously braided material incorporating between 72 and 288, or between about 144 and 192 filament "ends" in a 1-over-1, 1-over-2, 2-over-2 or other pattern. With (superelastic) Nitinol, the wire is advantageously between about 0.001 and about 0.003 inches in diameter. In which case, a supple and relatively "smooth" matrix surface is provided from which to construct the flexible funnel-trap architecture shown and described. The value of such a surface is in its atraumatic aspect and/or ability to help guide an IVC filter interface into position for capture even if it is oriented off-angle. Still, other wire sizes and/or end counts in a braid or other construction options are possible as well.

To assist with target device capture or recapture, the funnel trap structure 30 may be selectably directable. As indicated by the arrows in FIG. 2, the material from which it is made can be heatset or otherwise configured to provide a bias in an angular direction. The angle of deployment may be selectable or fully straightened by relative position of a core member or obturator (not shown) or by a sleeve or catheter sheath as further described. Further positioning may be achieved by rotating the device as further illustrated. Alternatively, a curved, "L" or "J" shaped wire may be received within a lumen of shaft 34 that can be passed up to and/or through to the inside of the funnel trap structure. Made of superelastic Nitinol (or other) wire, this member can be used to selectively shape or direct the device end. Likewise, a shaped catheter or sheath can be employed for such purposes.

Other device articulation options for selecting the angular orientation of the funnel-trap portion of the device are possible as well. Any of a variety of steerable or directable catheter-type technologies (reliant on pull-wires or otherwise) can be incorporated in shaft 34 for such purposes. Examples include the mechanisms described in U.S. Pat. Nos. 4,723,936; 4,960,411; 6,251,092 and 8,273,073 each incorporated herein by reference in its entirety for such description.

Figure 3:
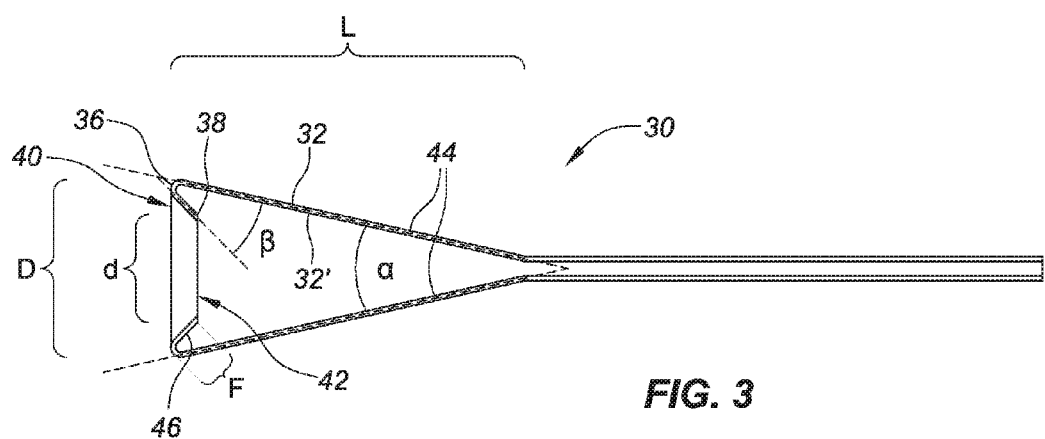
FIG. 3 is a side-sectional view of a converted preform (i.e., a finally shaped funnel section of the subject device) after heatsetting.

The "funnel trap" may be generally frusto-conical in shape as shown or otherwise configured. With an outer conical shape (i.e., a triangular shape in cross section as shown in FIG. 3) the structure is highly supportive for any necessary or desirable tissue discretion that might need to occur to free an emplaced filter. Moreover, such a shape provides a flexible "waist" section 48 for the directable feature(s) noted above. Still, the device may be bowed outward along its sides or otherwise configured without departing from claimed inventive aspects or variations.

Importantly, the distal rim opening 40 of the structure is larger than the more proximal rim opening or aperture 42 to operate in guiding filter engagement feature(s) or enlargement 24/24' (as shown) past the proximal opening or aperture into a pocket (P) where it is captured and subsequently locked upon advancing sleeve 50.

Such a pocket is formed between braid walls 44 and bend or fold 38 in the braid, for which the fold optionally serves as an abutment feature with an edge or shoulder of nubbin/bump 24/24' when the funnel trap section 30 is compressed or collapsed. To ensure capture, the sleeve 50 may be advanced fully over trap 30 before withdrawal into a separate catheter. In other words, in some embodiments, advancing sleeve 50 over funnel section 30 "closes the trap" and securely captures the implant to be retrieved.

Sleeve 50 may be a dedicated part of system 100 or it may be a catheter or so-called jugular access sheath. After the medical device (as in the illustrated case a temporary IVC filter) is covered by advancing the sleeve 50 over it, then—typically—the medical device is retrieved by withdrawal into this sleeve, catheter or sheath 50 or another catheter (not shown). Any or all such activity may be visualized fluoroscopically by a physician by way of marker features 24/24' and 52 and/or others as may be conveniently provided.

Notably, system 100 may be used identically when capturing a filter 10 with a typical hook end 12. However, the additional bulk/lateral extension of the hook may necessitate use of a relatively larger sleeve or catheter 50 for locking.

In the various system architectures, the catheter/pusher shaft 34, sleeve 50 or other catheters or sheaths used in or with the system may comprise a simple extrusion (e.g., PTFE, FEP, PEEK, PI, etc.) or may be constructed using conventional catheter construction techniques and include a liner, braid support and outer jacket (not shown), metal hypotube, etc. Further, the filter frame may be constructed using conventional laser cutting and electropolishing techniques and/or be otherwise constructed. In embodiments intended for tracking through a guide/delivery catheter without an incorporated sheath, a loading sheath may be employed. Any such loading sheath may be splittable. Other typical percutaneous access instruments (such as wires, etc.), valves and other hardware may also be employed in connection with the invention embodiments, including medical treatment methods.

The funnel-trap structure 30 can be made as a subassembly and attached to its catheter/pusher shaft 34. PCT publication PCT/US2014/042343 (WO2014201380) and U.S. patent application Ser. No. 14/569,500, each incorporated by reference in its entirety detail optional steps in the manufacture of a braid preform of the funnel-trap portion 30 of the final device as shown if FIG. 3.

Here, inner and outer layers of braid 32 are shown heatset using conventional techniques (e.g., in a furnace, salt pot, etc.) in a funnel shape with distal bends 36 in the braid wire forming an outer rim 40 with a large(r) distal opening or aperture. Inner or proximal bends 38 form an inner rim 42 with a small(er) more proximal opening or aperture. Stated otherwise, the braid used to construct the funnel-shape trap is folded back (e.g., in a flap 46) at the distal opening to provide a more proximal opening or aperture. Likewise, the braid is folded over or back to define the proximal opening or aperture.

For IVC filter retrieval, the funnel-trap portion 30 shown may have a diameter (D) from about 5 mm to about 20 mm, or more preferably about 10 to about 15 mm (i.e., size in a range to work within average size human IVCs where such vessels are reported as having a mean diameter of 20 mm within a range of 13 to 30 mm). A length (L) may range from about 10 mm to about 30 mm. An overall cone angle ($\alpha$) between braid walls 44 may be between about 30 and about 90 degrees. An angle ($\beta$) of bend 36 between braid wall 44 and flap 46 may be between about 0 and about 60 degrees and flap length (F) may be between about 1 and about 10 mm in length. Overall, an opening diameter (d) may be between about 5 and about 95 percent of diameter (D) depending on the selected combination of the noted variables (i.e., d, D, L, F, $\alpha$ and $\beta$). At the lower end of this range, the inner "opening" may be substantially closed such that must be pushed-open to receive the proximal engagement feature(s) of the implant during retrieval. At the higher end of the range, the flap may lie completely along or in-line with the outer layer(s) of the device. The configuration selected will depend upon the type of capture approach selected as further detailed herein. The opening 40 of the funnel trap may be set perpendicular relative to a device axis (A) as shown. Otherwise, it may be angled or have a more complex shape as described in connection with the above-referenced U.S. patent application Ser. No. 14/569,500 incorporated herein by reference.

As shown in FIG. 4, embodiments hereof may include a support member 110 including elongate members 112*a*, 112*b*, etc. set within the funnel trap section or portion of the device to support distal rim 40. This example shown in cross section may have eight such elongate members connected with four each to a nested or stacked hub portion (not shown). The support member(s) may alternatively or additionally be interposed between braid layers 32, 32". Further details of possible support member constructions and/or placements are set forth in PCT Patent Application No. PCT/US15/65025 and U.S. patent application Ser. No. 14/965,500, both of which are titled "IVC Filter Retrieval Systems with Interposed Support Members," and both of which are incorporated by reference herein in their entireties and for all purposes.

In FIG. 4, the system 200 shown includes components as discussed above along with the addition of a line, fiber, filament, fibril, thread, yarn or strand 210 serving as a tether 220. In one example, the strand element 210 (as a yarn or thread) is provided as a braided or plaited suture material. Ultra-high-molecular-weight polyethylene (UHMWPE) suture material may be selected for such purpose based on its strength, limited stretch and biocompatible characteristics. Other polymer fiber or metal filament (e.g., Nitinol) options are possible as well.

In any case, the tether can serve any number of purposes. In one example, the tether may hold or stabilize the inner flap 46 from pulling out or everting if the medical device 10 to be captured is one that includes a hook interface 12. A hook 12 can be captured by the funnel trap structure upon passing into or though the proximal rim opening 42. The hook may catch on a crossing filament as discussed further below or along the rim. For such purpose, the rim may be supported or supplemented with a ring 230 interposed between braid layers 32/32'. The ring may be defined by a portion of the strand 210 as further described below or otherwise.

In another example, the tether 220 may be used for actuation of the rim opening or aperture 42. When the ring 230 is in the form of a cinchable loop or lasso as part of the strand, the tether portion 220 of the strand can be used to close the associated aperture 42. (Examples of such loop or lasso constructions are discussed further below).

Figure 10:
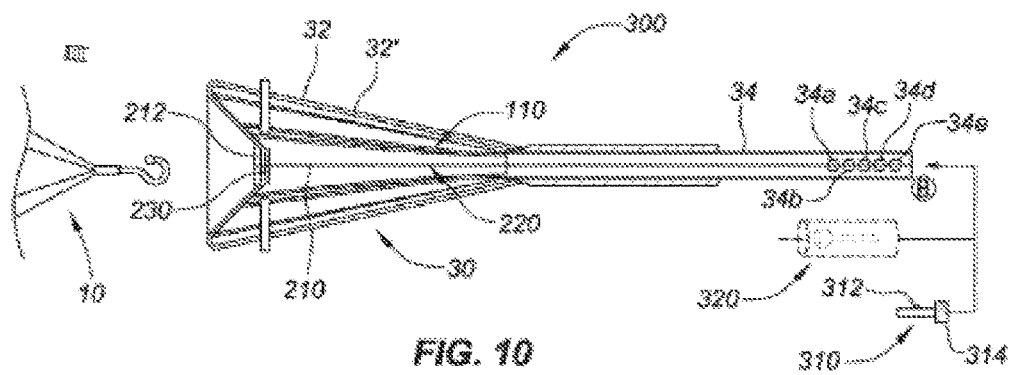
FIG. 10 is a side sectional view of a retrieval system embodiment including crossing member(s) and an optional tether.

The tether may be actuated (e.g., pulled) using a handle interface (e.g., as shown in FIG. 10). Alternatively, the tether may be affixed anywhere proximal to the funnel trap section 30 and still be used to close a lasso interface for medical device capture. Even if attached at or adjacent to point (A) in FIG. 4, when sheath 50 is advanced as shown over the funnel trap section 30, the braid defining the funnel trap collapses or compresses with the angle of its included wires changing. This causes the funnel section to lengthen. With the tether position fixed, it effectively "pulls" on any lasso member included at the proximal aperture closing it. All such action is indicated by arrow sets 1, 2, 3 in FIG. 4.

The so-called lasso may be included at an intermediate stage of production of the system 200. FIG. 5 shows a loop or lasso 232 configuration as further described in connection with FIG. 7A. While the loop 230 strand may be threaded into place at the wire bend or fold 38, it is more efficiently installed by pulling apart or folding back braid layer 32 and 32' and inserting it there between. Then, the braid configuration shown is flipped back so that flap section 46 is once again inset within the (optionally) conical shape of the funnel.

As shown in FIG. 7A, a loop pattern 232 is formed that includes a ring 230 and two exit legs or lengths 222*a*, 222*b*. These lengths may extend substantially as indicated by the arrows and used as tether members, tied-off to one another and trimmed, one may be tied-off to another and trimmed with the other used at a longer length, etc.

In FIG. 5, loop pattern 232 is set in place between braid layers 32, 32' with its two ends 222a, 222b exiting the same space or nearby spaces in the braid as shown. Pulled as a tether 220, loop 230 inside aperture 42 is cinched or closed down (as indicated by arrows 5 and 3, respectively).

Another approach in defining a cinchable loop is to use a slipknot or eyelet in the strand so that a single entry/exit member can be used passing through the braid. FIG. 6 is a side view of a portion of a suture or other fiber strand 210 setup for splicing-in such an eyelet. Sometimes the type of splice 240 to be constructed with the setup shown is referred to as a "long buried" splice. With hollow braided (in this case) suture material, an elongate tail 242 section of the material can be drawn through a splice channel 244 opened in the strand of material to define an eye or eyelet region 246. A needle or wire tool 248 may be used to draw the tail through the body of the strand 210.

With a ratio of splice length (SL) to strand diameter (d) of about 35 to 70 times or greater, (i.e., SL in the case of the suture material described below of about 5 to 6 mm long) splice strength on par with the native material can be achieved. For added security, the splice channel or section 244 can be further stabilized by biocompatible glue, laser welding or heat staking. Still further, any remaining tail 242 length of the splice can be melt-formed into a ball (not shown) that will not pull through the braided body. Other variations in the splicing procedure may include removing a number of filaments from the tail section to reduce the splice bulk. However, when dealing with fine suture (e.g., on the order of about 0.008 to about 0.012 inches (or about 0.2 to about 0.3 mm) in diameter with as few as 6 or 8 braided threads as advantageously used in embodiments hereof) such activity may be avoided.

Referring specifically to FIG. 7B, it illustrates loop pattern 234 constructed with such a splicing approach. A single strand 210 passes through the eyelet 246 formed by splicing. The end length 222 may serve for a tether or other features as further described.

FIG. 7C shows a loop pattern or approach 236 where an eyelet 248 is formed by splitting or passing the strand 210 through itself. The end of the strand opposite any retained end length 222 may be tied-off by a knot, weld or glue bead 250.

FIG. 7D presents yet another loop or lasso pattern 236. Here, two strands 210a and 210b are provided to encircle a funnel aperture 42. This approach may offer improved syncing around the fold 38 in which it may be placed. However, with as many as four tether ends 222a-222d to manage for assembly, other options may be preferred.

Figure 8:
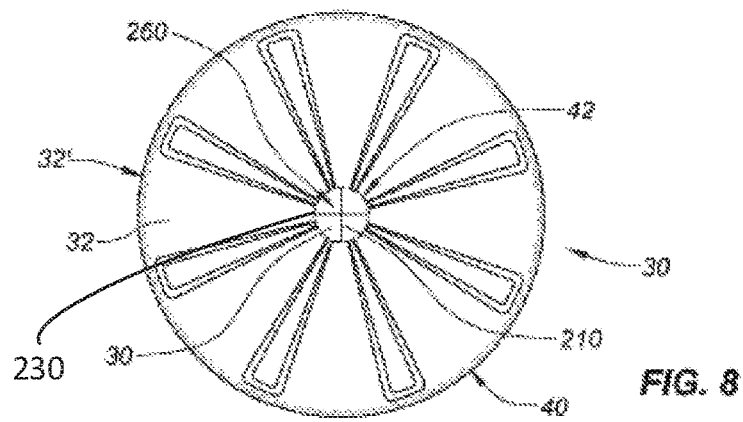
FIG. 8 is an end view of a funnel trap with crossing member and tether installed.

FIG. 8 is an end view of a funnel trap 30 variation that may include a ring 230, optionally in the form of a cinchable loop or lasso. Such a construction may be placed between braid layers 32/32'. Or at least one strand 210 may be used to define a cross-hairs type structure 260. More generally, one, two or more aperture crossing strands may be installed or threaded through or with the braid to serve as a filter hook 12 capture interface.

With multiple crossing strands or members, a "web" for implant capture may be defined. The web may use regularly (i.e., consistently) spaced members. Or it may be asymmetrical. The web may include two segments crossing in an "X" pattern (e.g., as shown in FIG. 8). Another example may have three segments defining a "Y" shape. Yet another example pattern is in the shape of a trefoil knot. Still others options are possible as well.

Figure 9A:
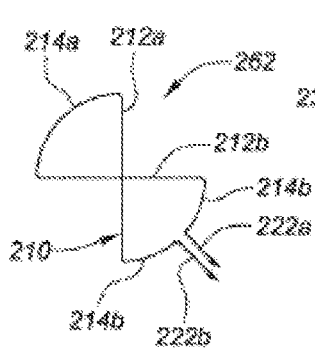
FIGS. 9A-9C are top or end view illustrations of various crossing member and tether construction options.
Figure 9B:
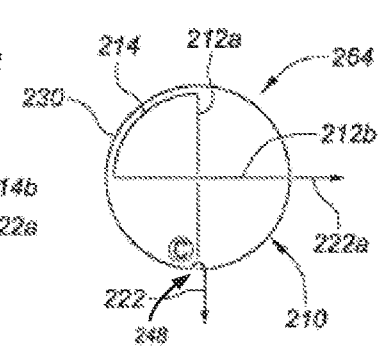
Figure 9C:
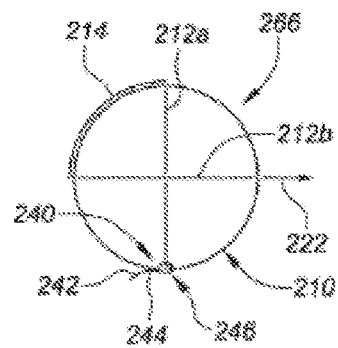

Particular tying or threading patterns for X- or crossing-type webs are presented in FIGS. 9A-9C. A simple cross or X type interface (i.e., without a surrounding loop or ring) may be constructed with a pattern 262 as show in FIG. 9A. As sort of a figure-eight threading pattern through the braid (with crossing sections 212a and 212b and curve or turn sections 214a, 214b) set between or outside braid layers 32, 32' includes two end lengths (222a, 222b). These may be tied off to one another in a knot (not shown), they may pass proximally to a tie-off or glue-in point, or be otherwise managed or handled.

FIG. 10 illustrates an example of a proximal end glue-in attachment point or zone (B) where shaft 34 includes ports 34a-34f. These ports may receive adhesive for an improved physical lock with shaft body and/or simply provide visual indication of formation of an adequate length glue joint to hold tether member(s) securely within the shaft.

FIG. 9B shows an alternative tie pattern for a loop and crosshair arrangement 264. The loop or ring 230 defined (when placed between braid layers) supports any filter (or other implant) hook received in or around the rim of the funnel trap device. With such a ring in place, a hook cannot simply pull through a number of captured or entrained braid filaments (a consideration when using fine Nitinol or other filaments in the braid). Rather, the hook would have to pull past the strand 210 itself (which is also supported by braid all around). Regardless, the hook may sometimes instead catch or locate upon the crossing members 212a, 212b of the pattern. They are supported from pull-out by the ends 222a, 222b that may be secured to one another by tying or otherwise as per variations discussed above.

As for other details of pattern 264, note the looping-around or intertwining of strand sections indicated at (C) that may assist in providing a more stable loop structure. Also, note the center region in which the horizontal member 214b (as oriented in the view) appears to cross over the vertical member 214a, and the strand portion adjacent extensions 222a under adjacent loop 230 section. Such up/down or over/under weaving may advantageously be employed to control strand portion position or placement within the finally constructed device.

Similar or related weaving is shown for pattern 266 shown in FIG. 9C. What differs primarily here is the use of a strand 210 with a splice 240 and splice-defined eyelet 248 so that a structure similar to that in FIG. 9B can be produced with a single end 222 where this end may ultimately serve as a tether or be tied-off at the aperture (to the strand, adjacent braid or otherwise).

Referring again FIG. 10, it provides a side sectional view of a retrieval system embodiment 300 including crossing member(s) 212, a ring 230 around proximal opening rim 42, and an optional tether(s) 220. The tether glue-in approach illustrated has already been discussed. Also noteworthy is the manner in which the setup is configured to release the tether if disengagement of a/the filter is desired. Simply by cutting shaft 34, the tether 210 is released and can be pulled free of filter hook 12 engagement. In another arrangement, a plug 310 may be used to secure or hold the tether in place in system 300 (or system 200) until removed. The plug may be press fit (lightly so as to allow removal), threaded or held with a detent 312 in place. A textured or knurled grip 314 may be provided for user-interface purposes. Other options are possible as well.

But once the plug is pulled or the shaft is cut, tether 210 is released. Especially when a spliced-eyelet tether is used with its loop or ring set between braid layers, such release does not risk losing the tether strand 210 altogether from system 200 and/or 300.

Also notable is that system 300 can advantageously be used to capture a filter 10 without a locking catheter (note that none is shown in FIG. 10). Still, cover and withdrawal of any captured IVC filter will commonly be accomplished in connection with a commercially available catheter or sheath.

Still further, an optional handle 320 (indicated by dashed line at small scale) may be included in the system for any desired tether manipulation. With such a handle, an opening interface selected from any of the patterns presented in FIGS. 7A-7D, 9A-9C or related may be closed by pulling the tether through handle manipulation (e.g., via a wheel, thumb slide or other user interface feature). Also, the handle may be configured to release tether 210 like plug 310 described above and/or let-out some portion of tether length (e.g., up to about 0.5 inches or about 10 mm to about 15 mm or more) to allow flap 46 and aperture 42 eversion for any efforts that may be desired to release a hook 12 from the system.

Methods

Figure 11:
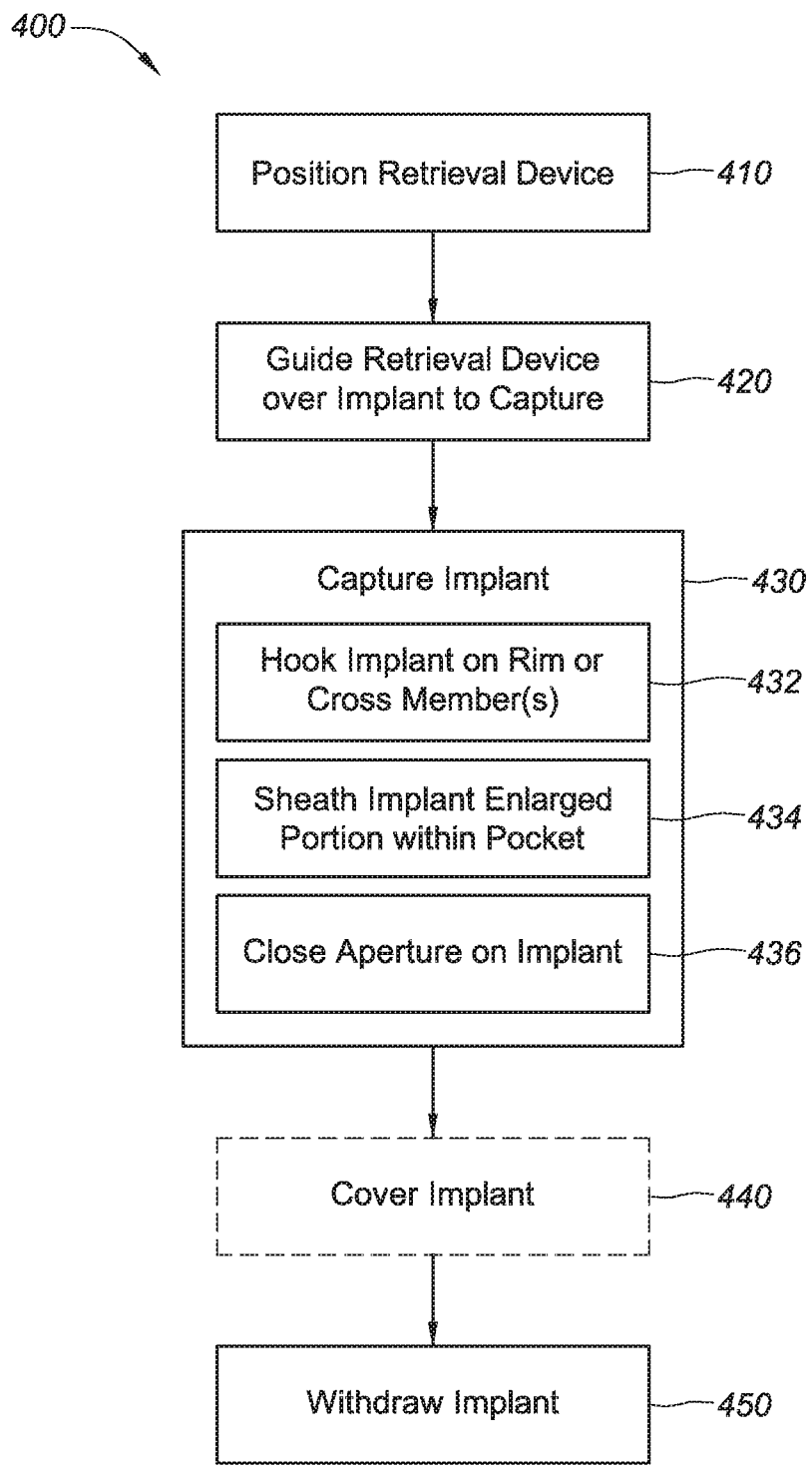
FIG. 11 is a flow diagram depicting an example embodiment of a method of use.

Various methods 400 of use can be defined in connection with the subject funnel trap embodiments 100, 200 or 300 or related medical device hardware. FIG. 11 is a flow diagram depicting one example embodiment of a method of use. Vascular access, medical imaging and positioning of the selected device adjacent to an implant or foreign body to be retrieved in the patient's vasculature are steps common to the methods. For example, see 410 in FIG. 11. Such positioning 410 is achieved by or after passing the funnel trap device through a sleeve in the form of a vascular access sheath or catheter.

Likewise, at 420, the methods include positioning the funnel trap device over the proximal portion of the element to be captured. In doing so (i.e., for the case of filter retrieval), the proximal capture interface of the filter will pass first through a distal aperture and then through the proximal aperture of the funnel-trap device. Due to the braided construction offered, such passage may be regarded both as protected (i.e., as the implant capture feature of the implant is within the boundary defined by braid) and self-guided (i.e., as the capture feature moves past or along the inner flap section of the funnel trap).

At 430, a number of capture options are possible depending on the system selected for use. Per option 432, the proximal interface may be a hook captured by a crossing member or along the rim interface at the proximal aperture of the funnel trap retrieval device. As another option 434, a loop or lasso feature at the proximal aperture may be cinched or tightened around the implant capture feature (be it a hook or other enlarged portion of an IVC filter). As yet another option 436 (i.e., in connection with advancing a locking sheath or catheter), the implant capture feature may be secured within a pocket of the device at or adjacent to the aperture and its rim.

After any such action, a/the catheter is typically advanced to cover the IVC filter at 440. During such advancement, tissue may separate from the body or legs of the filter (i.e., if this is the type of implant being capture, other possibilities include lost or stray embolization coils, part of a Central Venous Catheter (CVC) or line, etc). Finally, at 450, the filter (or other medical device) is withdrawn through a catheter.

Both the advancement to cover the implant (or other device to be retrieved or recovered) and withdrawal may take place in connection with one catheter. However, when a separate locking catheter is provided (e.g., in connection with system 100 for the approach in 434) an inner locking catheter will typically be what is advanced over the implant or device to be retrieved, and it will be withdrawn—together with the implant or device retrieved—out through an outer access catheter or sheath (i.e., the catheter or sheath originally used to achieve vascular access).

Clearly, a single-catheter approach can save procedure and/or fluoroscopy time. Systems 200 and 300 may be better suited to realize such advantages in view of their additional implant or device (e.g., IVC filter) capture features they possess as variously described above. However, each of the system embodiments described herein presents its own unique advantages that argue for its use and clinical relevance and/or adoption, especially in comparison to known retrieval devices and approaches.

Variations

The subject methods, including methods of use and/or manufacture, may be carried out in any order of the events which is logically possible, as well as any recited order of events. Embodiment methods may include any of a hospital staffs activities associated with device provision, implant positioning, re-positioning, implant or device retrieval and/or release.

Furthermore, where a range of values is provided, it is understood that every intervening value, between the upper and lower limit of that range and any other stated or intervening value in the stated range is encompassed within the invention. Also, it is contemplated that any optional feature of the inventive variations described may be set forth and claimed independently, or in combination with any one or more of the features described herein.

Though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention.

Reference to a singular item includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity. Accordingly, the breadth of the different inventive embodiments or aspects described herein is not to be limited to the examples provided and/or the subject specification, but rather only by the scope of the issued claim language.

The invention claimed is:

1. An apparatus for delivery or retrieval of a vascular medical device, the apparatus comprising:
an elongate shaft having an axis and a flexible distal extension, the flexible distal extension comprising a braid folded back at a first fold to form two layers;
upon deployment, the two layers of the flexible distal extension are folded-hack inwardly at a second fold to form a funnel having a distal opening and a proximal opening, the proximal opening being formed by the first fold, the proximal opening configured to receive therethrough a portion of the medical device for securing the medical device;
a tether disposed between the two layers of the braid and around a portion of the proximal opening; and
an elongate sleeve having a lumen, wherein the elongate shaft and the flexible distal extension are within the lumen of the elongate sleeve.

2. The apparatus of claim 1, wherein the distal extension is selectable in angular orientation.

3. The apparatus of claim 1, wherein the two layers of braid are bonded to the shaft.

4. The apparatus of claim 1, further comprising the medical device.

5. The apparatus of claim 4, wherein the medical device is an inferior vena cava filter.

6. The apparatus of claim 1, wherein the elongate sleeve is sized to secure the portion of the medical device in a pocket within the distal extension.

7. The apparatus of claim 1, wherein the tether is configured to at least partially close the proximal opening upon actuation.

8. The apparatus of claim 7, wherein the tether is connected to the elongate shaft proximal to the proximal opening.

9. The apparatus of claim 8, wherein the tether is connected at a proximal end region of the elongate shaft.

10. The apparatus of claim 9, further comprising a user interface at a proximal end region of the shaft and connected to the tether to actuate the tether for closing or releasing the proximal opening, the user interface selected from a handle and a plug received by the elongate shaft.

11. The apparatus of claim 1, wherein the funnel has a cone angle between 30 to 90 degrees when deployed.

12. The apparatus of claim 1, wherein the tether is configured as a lasso.

13. The apparatus of claim 1, wherein the distal opening is larger than the proximal opening.

14. The apparatus of claim 1, wherein the tether and the flexible distal extension exit out of the elongate shaft at a same opening, and wherein the flexible distal extension encloses a portion of the tether that extends out of the elongate shaft.

15. The apparatus of claim 1, wherein the tether forms a cross-hair type structure in the proximal opening.

16. An apparatus for delivery or retrieval of a vascular medical device, the apparatus comprising:
an elongate sleeve having a lumen;
an elongate shaft slidably positioned within the lumen of the elongate sleeve;
a flexible extension attached to the elongate shaft, the flexible extension comprising a braid folded back at a first fold to form two layers of the braid, and upon deployment, the two layers of the flexible extension form a braided funnel having an inwardly-folded-hack portion with a distal opening at a second fold and a proximal opening at the first fold, the proximal opening being displaced from an end of the elongate sleeve and sized to receive a portion of the medical device therethrough for securing the medical device; and
a tether disposed between the two layers of the braid and around a portion of the proximal opening.

17. The apparatus of claim 16, wherein the funnel comprises a heatset material that is biasable in an angular direction.

18. The apparatus of claim 16, wherein the tether encircles the proximal opening.

19. The apparatus of claim 16, further comprising:
a user interface at the proximal end of the elongate shaft and
wherein the tether is connected to the proximal opening and to the user interface, wherein the user interface is configured to actuate the tether for closing or opening the proximal opening, wherein the user interface is selected from a group consisting of a handle, a plug, a wheel, and a thumb slide.

20. The apparatus of claim 16, wherein the tether and the flexible extension exit out of the elongate shaft at a same opening, and wherein the flexible extension encloses a portion of the tether that extends out of the elongate shaft.

21. The apparatus of claim 16, wherein the tether comprises a strand that forms a loop at the proximal opening and an eyelet.

22. The apparatus of claim 16, wherein the tether forms a cross-hair type structure in the proximal opening.

* * * * *